United States Patent [19]

Baltz

[11] 4,159,226

[45] Jun. 26, 1979

[54] METHOD OF OBTAINING STREPTOMYCES PROTOPLASTS CAPABLE OF EFFICIENT CELL REGENERATION

[75] Inventor: Richard H. Baltz, Indianapolis, Ind.

[73] Assignee: Eli Lilly and Company, Indianapolis, Ind.

[21] Appl. No.: 812,084

[22] Filed: Jul. 1, 1977

[51] Int. Cl.² .............................................. C12K 1/02
[52] U.S. Cl. .................................... 195/79; 195/78; 195/80 R; 195/1
[58] Field of Search ...................... 195/1, 80 R, 78, 79

[56] References Cited

PUBLICATIONS

Okanishi et al., J. Gen. Microbiol, vol. 80, 389–400 (1974).
Villanueva et al., Yeast Mould and Plant Protoplasts, Academic Press, pp. 275–283 (1973).

*Primary Examiner*—Alvin E. Tanenholtz
*Attorney, Agent, or Firm*—Nancy J. Harrison; Arthur R. Whale

[57] ABSTRACT

A method of obtaining Streptomyces protoplasts which are able to regenerate viable cells with high efficiency is disclosed. The method involves growing Streptomyces cells to a particular physiological state, the transition phase between the exponential and stationary growth phases, and then forming protoplasts. The physiological state of the cells at the time of protoplast formation is crucial for efficient cell regeneration. Protoplasts obtained by this method enhance the use of protoplast-fusion techniques to effect genetic exchange within the genus Streptomyces, thereby facilitating the construction of hybrid or recombinant Streptomyces strains with useful properties.

32 Claims, No Drawings

METHOD OF OBTAINING STREPTOMYCES PROTOPLASTS CAPABLE OF EFFICIENT CELL REGENERATION

BACKGROUND OF THE INVENTION

Cell-fusion techniques have been devised for several eucaryotic cell systems to facilitate formation of hybrid cells. Genetic exchange mediated by cell fusion had not been demonstrated with procaryotic microorganisms until Shaeffer et al. and Fodor and Alfoldi devised techniques involving fusion of protoplasts and regeneration of cells of the procaryotic genus Bacillus, [P. Schaeffer et al., Proc. Nat. Acad. Sci. 73, 2151–2155 (1976) and K. Fodor and L. Alfoldi, Proc. Nat. Acad. Sci. 73, 2147–2150 (1976)]. Still more recently, it was discovered that protoplastfusion-induced genetic exchange, including genetic recombination, is possible within the economically important genus Streptomyces [Baltz and Godfrey, copending patent application titled METHOD OF FACILITATING GENETIC EXCHANGE IN STREPTOMYCES BY PROTOPLAST FUSION Ser. No. 812,097, filed this even date].

A crucial step in the process of protoplast-fusion-induced genetic exchange or genetic recombination is recovery of variable cells from the fused protoplasts. In the case of Bacillus, the fused protoplasts were reverted to viable cells under conditions that had been well worked out previously for single cells. In the case of the filamentous Streptomyces, however, very little was known about the process of forming protoplasts capable of reverting to viable cells. M. Okanishi, et al. [J. Gen. Microbiol. 80, 389–400 (1974)] reported that S. griseus and S. Venezuelae protoplasts could be formed from cells taken from a mid-exponential growth phase by treatment with lysozyme and lytic enzyme No. 2 in a hypertonic medium and that these protoplasts could regenerate viable cells efficiently. They also reported that cells from stationary phase did not form protoplasts well at all. In contrast to Okanishi's report, I have discovered that Streptomyces cells from the mid-exponential growth phase revert very poorly; but that cells from the transition growth phase, which follows the classical exponential phase but precedes the stationary growth phase, regenerate very efficiently. My discovery relates, therefore, to the optimum conditions for preparing Streptomyces protoplasts which are capable of efficiently resynthesizing cell walls and regenerating viable cells. My technique increases the probability of detecting specific genetic exchange between different Streptomyces strains by protoplast fusion. Genetic exchange is an important tool for increasing variability within species which produce economically and therapeutically important metabolites, such as antibiotics. Industrial applications of this tool include constructing strains which produce high levels of specific metabolites such as antibiotics, antitumor agents, enzymes and other microbial products having useful properties, and constructing hybrid species which produce novel metabolites with useful properties.

DETAILED DESCRIPTION

This invention relates to a method of obtaining Streptomyces protoplasts which are capable of regenerating viable cells. The method involves growing Streptomyces cells to a particular physiological state and then forming protoplasts. The particular physiological state relates to a segment of the growth phase in which I have discovered that 1) the Streptomyces cells have the ability to form protoplasts efficiently and 2) the protoplasts formed have the ability to regenerate viable cells efficiently. This particular state, the most competent state, is the transition phase between the exponential and stationary phases.

The most competent state can be determined by monitoring the Streptomyces growth cycle. The cycle can be monitored by any one of a number of well known techniques. A convenient method is by turbidometric assay in a complex medium containing glycine. Using the turbidometric assay, the growth phases can be defined by measuring changes in optical density (OD). A suitable turbidometric measurement, such as absorbancy at 600 nm ($A600$), can be used to measure changes in OD.

In general, Streptomyces species undergo fairly rapid exponential growth with cell-doubling times ranging from about 1.5 hours to several hours at low cell density ($A600$ less than about 1.5) in soluble complex media. As cell growth reaches $A600$ readings of from about 1.5 to 4.0, cells enter a transition phase which precedes the stationary growth phase. The transition phase may last from 2 to 24 hours, and cell mass may increase by about 50% to 6-fold during this growth phase, depending on the species in question.

During the course of growth through these various phases, physiological changes take place which influence dramatically the ability to form protoplasts which are capable of reverting to viable cells. Protoplasts are formed typically by treatment of mycelial cells with lysozyme in a hypertonic medium.

I have found that cells from the early exponential growth phase (i.e., $A600$ of from about 0.5 to about 0.2, or even up to 0.4 with some Streptomyces) do not form protoplasts well. With S. fradiae, however, after the early exponential growth phase, there exists a transient period during which the cells can form protoplasts which will revert to viable cells: e.g., S. fradiae cells at $A600$ of about 0.4 can be converted to protoplasts, and the protoplasts will revert to viable cells fairly efficiently. This competency to regenerate cells, however, is rapidly lost as cells enter the mid-exponential growth phase.

In the mid-exponential growth phase (i.e., $A600$ of from about 0.7 to about 1.4), the Streptomyces cells will form protoplasts, but the protoplasts do not revert efficiently to viable cells. As cells enter the late exponential growth phase, however, they begin to regain the ability to form protoplasts which regenerate cells efficiently; and as they grow into the transition phase (an $A600$ of from about 2.0 to about 8.5) they become highly competent to form protoplasts which regenerate cells efficiently. Competency to regenerate then declines dramatically as cells enter the stationary growth phase.

A similar pattern is seen with S. griseofuscus and S. auerofaciens except that the transition phase preceding the stationary phase is much shorter.

My methods consists, therefore, of growing Streptomyces cells to the most competent state (the transition phase between the exponential and stationary phases), forming protoplasts, and allowing the protoplasts to revert to viable cells by plating on a suitable medium. My method, which facilitates efficient regeneration of cells from protoplasts, clearly enhances the probability of detecting genetic exchange, including genetic recombination, within the genus Streptomyces (see examples 4 and 5).

My method is intended to apply to many Streptomyces species. As discussed in further detail in Examples 1–3, my method has been demonstrated in *Streptomyces fradiae, Streptomyces griseofusus* and *Streptomyces aureofaciens.*

One streptomycete which has thus far failed to revert under these conditions is *Streptomyces cinnamonensis*, a strain which has been observed to produce potent autolytic activity after growth in complex medium supplemented with glycine.

Streptomyces species for which my method is preferred are those which produce antibiotics. Especially preferred Streptomyces species are those which produce aminoglycoside antibiotics, macrolide antibiotics, betalactam antibiotics, polyether antibiotics, or glycopeptide antibiotics.

Streptomyces species which are known to produce aminoglycoside antibiotics include, for example: *S. kanamyceticus, S. chrestomyceticus, S. griseoflavus, S. microsporeus, S. ribosidificus, S. flavopersicus, S. spectabilis, S. rimosus* forma *paromomycinus, S. fradiae* var. *italicus, S. bluensis* var. *bluensis, S. catenulae, S. olivoreticuli* var. *cellulophilus, S. tenebrarius, S. lavendulae, S. albogriseolus, S. albus* var. *metamycinus, S. hydroscopicus* var. *sagamiensis, S. bikiniensis, S. griseus, S. erythrochromogenes* var. *narutoensis, S. poolensis, S. galbus, S. rameus, S. olivaceus, S. mashuensis, S. hygroscopicus* var. *limoneus, S. rimofaciens, S. hygroscopicus* forma *glebosus, S. fradiae, S. eurocidicus, S. aquacanus, S. crystallinus, S. noboritoensis, S. hygroscopicus, S. atrofaciens, S. kasugaspinus, S. kasugaensis, S. netropsis, S. lividus, S. hafunensis,* and *S. canus.*

Streptomyces species which are known to produce macrolide antibiotics include, for example: *S. caelestis, S. platensis, S. rochei* var. *volubilis, S. venezuelae, S. griseofuscus, S. narbonensis, S. fungicidicus, S. griseofaciens, S. roseocitreus, S. bruneogriseus, S. roseochromogenes, S. cinerochromogenes, S. albus, S. felleus, S. rochei, S. violaceoniger, S. griseus, S. maizeus, S. albus* var. *coilmyceticus, S. mycarofaciens, S. hygroscopicus, S. griseospiralis, S. lavendulae, S. rimosus, S. deltae, S. fungicidicus* var. *espinomyceticus, S. furdicidicus, S. ambofaciens, S. eurocidicus, S. griseolus, S. flavochromogenes, S. fimbriatus, S. fasciculus, S. erythreus, S. antibioticus, S. olivochromogenes, S. spinichromogenes* var. *suragaenosis, S. kitasatoensis, S. narbonensis* var. *josamyceticus, S. albogriseolus, S. bikiniensis, S. cirratus, S. djakartensis, S. eurythermus, S. fradiae, S. goshikiensis, S. griseoflavus, S. halstedii, S. tendae, S. macrosporeus, S. thermotolerans,* and *S. albireticuli.*

Streptomyces species which are known to produce beta-lactam antibiotics include, for example: *S. lipmanii, S. clavuligerus, S. lactamdurans, S. griseus, S. hygroscopicus, S. wadayamensis, S. chartreusis, S. heteromorphus, S. panayensis, S. cinnamonensis, S. fimbriatus, S. halstedii, S. rochei, S. viridochromogenes, S. cattleya, S. olivaceus, S. flavovirens, S. flavus, S. fulvoviridis, S. argenteolus,* and *S. sioyaensis.*

Streptomyces species which are known to produce polyether antibiotics include, for example; *S. albus, S. hygroscopicus, S. griseus, S. conglobatus, S. eurocidicus* var. *asterocidicus, S. lasaliensis, S. ribosidificus, S. cacaoi* var. *asoensis, S. cinnamonensis, S. aureofaciens, S. gallinarius, S. longwoodensis, S. flaveolus, S. mutabilis,* and *S. violaceoniger.*

Streptomyces species which are known to produce glycopeptide antibiotics include, for example: *S. orientalis, S. haranomachiensis, S. candidus,* and *S. eburosporus.*

In order to illustrate more fully the operation of this invention, the following specific examples are provided.

EXAMPLE 1

*Streptomyces fradiae* was grown in trypticase soy broth (TSB) containing 0.4% glycine for 6 to 10 cell doublings. (Glycine at 0.4% increases the cell-doubling time during exponential growth from about 1.6 hours to 2.7 hours; higher concentrations are much more inhibitory). Specific growth phases were determined by optical density (OD) readings at an absorbancy of 600 nm (A600 on a Baush and Lomb spectrophotometer). Samples were removed from specific growth phases; cells were homogenized and washed two times by centrifugation, resuspending in medium P [M. Okanishi, et al., *J. Gen. Microbiol.* 80, 389–400 (1974)]. The washed cells were treated with lysozyme (1–2 mg/ml) in medium P for 1 to 2 hours at 34° C. The resulting protoplasts were washed 2 to 3 times by centrifugation, resuspending in medium P; the washed protoplasts were diluted in medium P and plated on R 2 medium (M. Okanishi et al., supra) which was modified in that it contained asparagine instead of proline as a nitrogen source. Regenerated cells which formed colonies were counted after 9 to 12 days incubation at 34° C. About one-half of the regenerated cells produced visible colonies in about 5 to 7 days on R 2 medium. Background counts (hypotonic conditions in Table 1) were determined either by diluting protoplasts in distilled water before plating on hypertonic medium (R2), or by diluting in hypertonic buffer (P) and then plating on a hypotonic medium containing 0.8% nutrient broth plus 4 mM $Ca(NO_3)_2$. A summary of results from four experiments is given in Table 1. Cells from early exponential phase (i.e., cell-doubling time=2.7 hr; see Expt. No. 1) were not converted to protoplasts efficiently at all. Even after 16 hours incubation at 34° C., only a fraction had been converted to protoplasts. At an A600 of 0.46, cells were converted to protoplasts in 1 to 2 hours, and these protoplasts regenerated viable cells fairly efficiently. This "competent state" is rapidly lost as cells enter the mid-to-late exponential growth phase (A600 reading of 0.7 to 1.4). As cells enter the transition phase between the exponential and stationary growth phases at an A600 of about 1.4, they continue to grow, but at a much slower rate (i.e., cell-doubling time of about 11.5 hours), and begin to regain a high degree of competency to regenerate viable cells from protoplasts. The highest values, $8.6 \times 10^7$ colony-forming units (cfu)/OD, represent about 40% of maximum viability. As the cells enter stationary phase at about A600>8.5, they rapidly lose the ability to regenerate viable cells from protoplasts. The frequency of regenerated cells/OD from protoplasts formed during the most competent state (A600 of 2 to 4) is at least 30-fold and 300-fold higher than from protoplasts formed during the mid-to-late exponential and stationary phases, respectively.

Table 1

| Expt. No. | Cell OD | Growth Phase | Protoplast Formation | Colony-Forming Units/OD Cells* Hypertonic Conditions | Hypotonic Conditions |
|---|---|---|---|---|---|
| 1 | 0.16 | Exponential | Very poor | ND** | ND |
| 1 | 0.18 | " | Very poor | ND | ND |
| 1 | 0.30 | " | Very poor | ND | ND |
| 1 | 0.32 | " | Very poor | ND | ND |
| 1 | 0.38 | " | Very poor | ND | ND |
| 2 | 0.46 | " | Good | $5 \times 10^7$ | $<1.1 \times 10^3$ |
| 2 | 0.72 | " | Good | $6.8 \times 10^6$ | $<6.4 \times 10^2$ |
| 2 | 1.46 | Late exponential | Good | $2.7 \times 10^6$ | $<3.4 \times 10^2$ |
| 3 | 1.4 | " | Very good | $4.5 \times 10^7$ | $2.1 \times 10^2$ |
| 3 | 2.2 | Transition | Very good | $8.6 \times 10^7$ | $3.2 \times 10^1$ |
| 3 | 3.7 | " | Very good | $8.6 \times 10^7$ | $6.8 \times 10^1$ |
| 3 | 8.5 | " | Very good | $6.5 \times 10^7$ | $8.7 \times 10^1$ |
| 4 | 9.0 | Stationary | Very good | $2.5 \times 10^5$ | $4.7 \times 10^3$ |

*OD cells determined before protoplast formation
**not determined

EXAMPLE 2

*S. griseofuscus* was grown in TSB containing 0.8% glycine, using the procedure of Example 1. Protoplasts were formed and plated as in Example 1, except that colonies were counted after 7 days. As seen with *S. fradiae* in Example 1, *S. griseofuscus* cells taken from the transition phase (A600 of about 3.5 to 5.0) form protoplasts and regenerate viable cells most efficiently (Table 2). The highest efficiency, $1.1 \times 10^8$ cuf/OD, represents nearly 100% regeneration of potential viable cells. Again, cells in the early exponential growth phase did not form protoplasts well, and protoplasts from the stationary phase yielded no detectable revertants (i.e., $<5.8 \times 10^3$ cfu/OD). The efficiency of regenerating stationary-phase protoplasts is thus $>10^4$-fold lower than the efficiency of regenerating transition-phase cells.

Table 2

| Expt. No. | Cell OD | Growth Phase | Protoplast Formation | Colony-Forming Units/OD Cells* Hypertonic Conditions | Hypotonic Conditions |
|---|---|---|---|---|---|
| 1 | .16 | Exponential | Very poor | ND** | ND |
| 1 | .23 | " | Very poor | ND | ND |
| 1 | .35 | " | Very poor | ND | ND |
| 1 | .42 | " | Very poor | ND | ND |
| 1 | .54 | " | Very poor | ND | ND |
| 2 | 1.14 | Late exponential | Good | $2.2 \times 10^7$ | $<4.4 \times 10^2$ |
| 2 | 2.4 | " | Good | $4.7 \times 10^7$ | $<2.1 \times 10^2$ |
| 2 | 3.81 | transition | Good | $9.1 \times 10^7$ | $<1.3 \times 10^2$ |
| 3 | 4.8 | " | Good | $1.1 \times 10^8$ | $<5. \times 10^2$ |
| 3 | 4.3 | stationary*** | Good | $<5.8 \times 10^3$ | $<5. \times 10^2$ |

*OD cells determined before protoplast formation
**not determined
***10 hrs beyond transition phase

EXAMPLE 3

*S. aureofaciens* was grown in TSB containing 0.4% glycine; protoplasts were formed and plated, using the procedure of Example 1 except that colonies were counted after 8 days incubation at 34° C. Again, as seen with *S. fradiae* in Example 1 and *S. griseofuscus* in Example 2, cells from the transition phase (A600 of about 2.0 in this case) form protoplasts which regenerate more efficiently than cells from the late exponential growth phase. As shown in Table 3, efficiency of regeneration at A600=2.4 was about 10 times greater than efficiency of regeneration at A600=0.6.

Table 3

| Expt. No. | Cell OD | Growth Phase | Protoplast Formation | Colony-Forming Units/OD Cells* Hypertonic Conditions | Hypotonic Conditions |
|---|---|---|---|---|---|
| 1 | 0.6 | Exponential | Good | $3.5 \times 10^5$ | $<8.3 \times 10^2$ |
| 1 | 1.24 | Late exponential | Good | $4.6 \times 10^5$ | $4.0 \times 10^2$ |
| 1 | 2.4 | Transition | Good | $3.4 \times 10^6$ | $2.1 \times 10^2$ |

*OD cells determined before protoplast formation

EXAMPLE 4

*Streptomyces fradiae* auxotrophic mutants were used. At least one parent strain contained two auxotrophic markers and a spectinomycin resistance (spc) marker. Each of the genetically-marked *S. fradiae* strains was grown in TSB containing 0.4% glycine. When growth reached an A600 of about 1.5 to 5, the mycelia were washed twice by centrifugation and were resuspended in medium P (M. Okanishi, et al., supra). Lysozyme (1 to 2 mg/ml) was added to the suspension. The suspended mycelial cells were incubated for 0.5 to 2 hours at 30° or 34° C. The resulting protoplasts were mixed (0.5 ml of each parent suspension). The mixture was washed several times by centrifugation, resuspending in medium P and finally resuspending in 0.1 ml of medium P. A solution of 40% polyethylene glycol (PEG) 6000 in medium P (0.9 ml) was added to the final suspension to induce cell-membrane fusion. Protoplast fusion was confirmed by phase-contrast microscopy. The fused protoplasts were immediately diluted into one of the following media: medium P containing 40% PEG, medium P, or distilled water. The dilutions were plated on medium R2 (Okanishi, et al., supra) to allow detection of recombination and regeneration of prototrophic recombinants. The R2 medium used contained asparagine instead of proline as nitrogen source. Recombinants were counted after 10 to 24 days incubation at 34° C. In many of the crosses the prototrophic recombinants were further tested for the presence of an unselected marker (spectinomycin resistance) to eliminate single mutant reversion artifacts. Additional controls were run to confirm recombination. Total recombinants are based on original volumes of mixed protoplasts which generally contained from about $10^8$ to about $10^9$ protoplasts/ml, as determined by direct counting in a hemocytometer.

A summary of several genetic crosses by protoplast fusion is given in Table 4.

Example 4 except that: (1) the TSB was supplemented with 0.8% glycine and (2) recombinant colonies were counted after 7 days incubation at 34° C. Results are summarized in Table 5. In all six conditions protoplasts were treated with PEG, diluted in medium P and plated on medium R2. In all cases, the frequency of genetic recombinants was from $10^3$ to $10^4$-fold higher than background prototrophic revertants.

Table 5

| Condition | Parental Markers | | Prototrophic Recombinants or Revertants/ml |
|---|---|---|---|
| | Parent 1 | Parent 2 | |
| 1 | met | arg | $3.1 \times 10^4$ |
| 2 | met | trp | $4.8 \times 10^3$ |
| 3 | arg | trp | $4.2 \times 10^4$ |
| 4 | met | — | $<10^1$ |
| 5 | arg | — | $1.0 \times 10^1$ |
| 6 | trp | — | $<10^1$ |

I claim:

1. A method of obtaining Streptomyces protoplasts which are capable of efficiently regenerating viable cells which comprises growing the Streptomyces culture to the transition phase between the exponential and stationary phases and then forming protoplasts.

2. The method of claim 1 which includes the addi-

Table 4

| Condition | Parental Markers ∇ | | PEG Treatment | Dilution Medium | Prototrophic Recombinants, or Revertants/ml Δ | Spectinomycin Resistant Prototrophs |
|---|---|---|---|---|---|---|
| | Parent 1 | Parent 2 | | | | |
| 1 | metA arg spc | metB | + | P + PEG | $2.4 \times 10^4$ | 6/7 |
| 2 | metA arg spc | metB | — | P | $6.6 \times 10^3$ | 8/8 |
| 3 | metA arg spc | metB | — | H$_2$O | $7.0 \times 10^1$ | 11/11 |
| 4 | metA arg spc | — | + | P + PEG | $<10^1$ | 0/0 |
| 5 | metA arg spc | — | — | P | $<10^1$ | 0/0 |
| 6 | metA arg spc | — | — | H$_2$O | $<10^1$ | 0/0 |
| 7 | — | metB | + | P + PEG | $2 \times 10^1$ | 0/3 |
| 8 | — | metB | — | P | $2 \times 10^1$ | 0/6 |
| 9 | — | metB | — | H$_2$O | $2 \times 10^1$ | 0/8 |
| 10 | metA arg spc | cysD | + | P | $1.1 \times 10^5$ | ND* |
| 11 | — | cysD | + | P | $<10^1$ | ND |
| 12 | metA arg spc | — | + | P | $<10^1$ | ND |

*Not determined.
ΔDetermined on R2 medium.
∇Marker designations are those of Hopwood, et al. [Bact. Rev. 37, 371–405 (1973)]. The metA, arg and metB markers are auxotrophic. The spc marker designates resistance to 50 μg/ml spectinomycin.

A lower, but significant, level of recombination was obtained by centrifuging the protoplasts and resuspending in medium P without PEG. This level of protoplast fusion is presumably due to the presence of Ca$^{++}$ in the buffer. Dilution of the protoplasts into distilled water reduced the number of recombinants by 100-fold. Virtually all of the genetic recombinants tested contained the spc marker from the strain carrying the metA arg markers, ruling out the possibility that reversion of the metB strain might account for the data. The doubly marked auxotrophic strain has never been shown to revert to prototrophy, thus eliminating reversion of this strain as an explanation of the results. The other controls in Table 4 give additional evidence that recombination does indeed take place after protoplast fusion. Upon recloning, all putative recombinants were shown to be stable. The *S. fradiae* strain used is one which produces the antibiotic tylosin. Many genetic recombinants of this *S. fradiae* strain were shown to be tylosin producers.

EXAMPLE 5

*Streptomyces griseofuscus* was used in these genetic crosses. The procedures were the same as those used in tional step of regenerating viable cells from the protoplasts formed.

3. The method of claim 1 wherein the Streptomyces is *Streptomyces fradiae*.

4. The method of claim 1 wherein the Streptomyces is *Streptomyces griseofuscus*.

5. The method of claim 1 wherein the Streptomyces is *Streptomyces aureofaciens*.

6. The method of claim 1 wherein the Streptomyces is *Streptomyces bikiniensis*.

7. The method of claim 1 wherein the Streptomyces is *Streptomyces lipmanii*.

8. The method of claim 1 wherein the Streptomyces is *Streptomyces candidus*.

9. The method of claim 1 wherein the Streptomyces is *Streptomyces tenebrarius*.

10. The method of claim 1 wherein the Streptomyces is *Streptomyces erythreus*.

11. The method of claim 1 wherein the Streptomyces is *Streptomyces clavuligerus*.

12. The method of claim 1 wherein the Streptomyces is *Streptomyces coelicolor*.

13. The method of claim 1 wherein the Streptomyces is *Streptomyces griseus.*

14. The method of claim 1 wherein the Streptomyces is *Streptomyces albofaciens.*

15. The method of claim 1 wherein the Streptomyces is *Streptomyces albogriseolus.*

16. The method of claim 1 wherein the Streptomyces is *Streptomyces albus.*

17. The method of claim 1 wherein the Streptomyces is *Streptomyces aquacanus.*

18. The method of claim 1 wherein the Streptomyces is *Streptomyces capreolus.*

19. The method of claim 1 wherein the Streptomyces is *Streptomyces cattleya.*

20. The method of claim 1 wherein the Streptomyces is *Streptomyces crystallinus.*

21. The method of claim 1 wherein the Streptomyces is *Streptomyces kanamyceticus.*

22. The method of claim 1 wherein the Streptomyces is *Streptomyces kasugaensis.*

23. The method of claim 1 wherein the Streptomyces is *Streptomyces kasugaspinus.*

24. The method of claim 1 wherein the Streptomyces is *Streptomyces kitasatoensis.*

25. The method of claim 1 wherein the Streptomyces is *Streptomyces lactamdurans.*

26. The method of claim 1 wherein the Streptomyces is *Streptomyces lasaliensis.*

27. The method of claim 1 wherein the Streptomyces is *Streptomyces lavendulae.*

28. The method of claim 1 wherein the Streptomyces is *Streptomyces lincolnensis.*

29. The method of claim 1 wherein the Streptomyces is *Streptomyces narbonensis.*

30. The method of claim 1 wherein the Streptomyces is *Streptomyces norboritoensis.*

31. The method of claim 1 wherein the Streptomyces is *Streptomyces orientalis.*

32. The method of claim 1 wherein the Streptomyces is *Streptomyces rimosus.*

* * * * *